United States Patent [19]
Pfeiler et al.

[11] Patent Number: 5,231,653
[45] Date of Patent: Jul. 27, 1993

[54] X-RAY DIAGNOSTICS INSTALLATION

[75] Inventors: Manfred Pfeiler; Gerd Wessels, both of Erlangen; Lothar Heinz, Neunkirchen A. Brand; Peter Hoebel, Buckenhof, all of Fed. Rep. of Germany

[73] Assignee: Siemens Aktiengesellschaft, Munich, Fed. Rep. of Germany

[21] Appl. No.: 855,164

[22] Filed: Mar. 20, 1992

Related U.S. Application Data

[63] Continuation of Ser. No. 624,572, Dec. 10, 1990, abandoned.

[30] Foreign Application Priority Data

Jan. 11, 1990 [EP] European Pat. Off. ......... 90100537.1

[51] Int. Cl.⁵ ............................................. H05G 1/08
[52] U.S. Cl. ...................................... 378/91; 378/98; 378/194; 378/196; 378/197
[58] Field of Search ......... 378/4, 15, 10, 99, 134-138, 378/91, 901, 117, 96, 114, 97, 147, 150, 151, 206, 208; 256/390.04, 390.07

[56] References Cited

U.S. PATENT DOCUMENTS

| | | | |
|---|---|---|---|
| 3,970,853 | 7/1976 | Kuhl et al. | 378/15 |
| 4,259,584 | 3/1981 | Krumme | 378/15 |
| 4,283,629 | 8/1981 | Habermehl et al. | 378/197 |
| 4,288,700 | 9/1981 | Grass et al. | 378/194 |
| 4,323,781 | 4/1982 | Baumann et al. | 378/15 |
| 4,624,007 | 11/1986 | Muranushi | 378/4 |
| 4,796,183 | 1/1989 | Ermert et al. | 378/4 |
| 4,802,197 | 1/1989 | Juergens | 378/197 |
| 4,864,142 | 9/1989 | Gomberg | 378/57 |
| 4,887,287 | 12/1989 | Cobben | 378/198 |
| 4,982,415 | 1/1991 | Shibata et al. | 378/15 |
| 5,077,771 | 12/1991 | Skillicorn et al. | 378/102 |

FOREIGN PATENT DOCUMENTS

| | | |
|---|---|---|
| 690656 | 4/1953 | United Kingdom . |
| 711887 | 7/1954 | United Kingdom . |
| 713055 | 8/1954 | United Kingdom . |
| 808611 | 2/1959 | United Kingdom . |

OTHER PUBLICATIONS

Siemens Brochure for Siremobil 4, Oct. 1987.

Primary Examiner—David P. Porta
Assistant Examiner—Kim-Kwok Chu
Attorney, Agent, or Firm—Hill, Steadman & Simpson

[57] ABSTRACT

A transmission link which couples data from a mobile x-ray apparatus to image electronics is provided with a data coupling, and a data plug is allocated to the x-ray apparatus and a data socket is allocated to the image electronics, such that data may be transmitted between the x-ray apparatus and the image electronics. The transmission link can include wireless transmission of image data from a mobile x-ray diagnostic apparatus, with an optical transmitter allocated to the x-ray apparatus and a wireless receiver allocated to the image electronics.

8 Claims, 1 Drawing Sheet

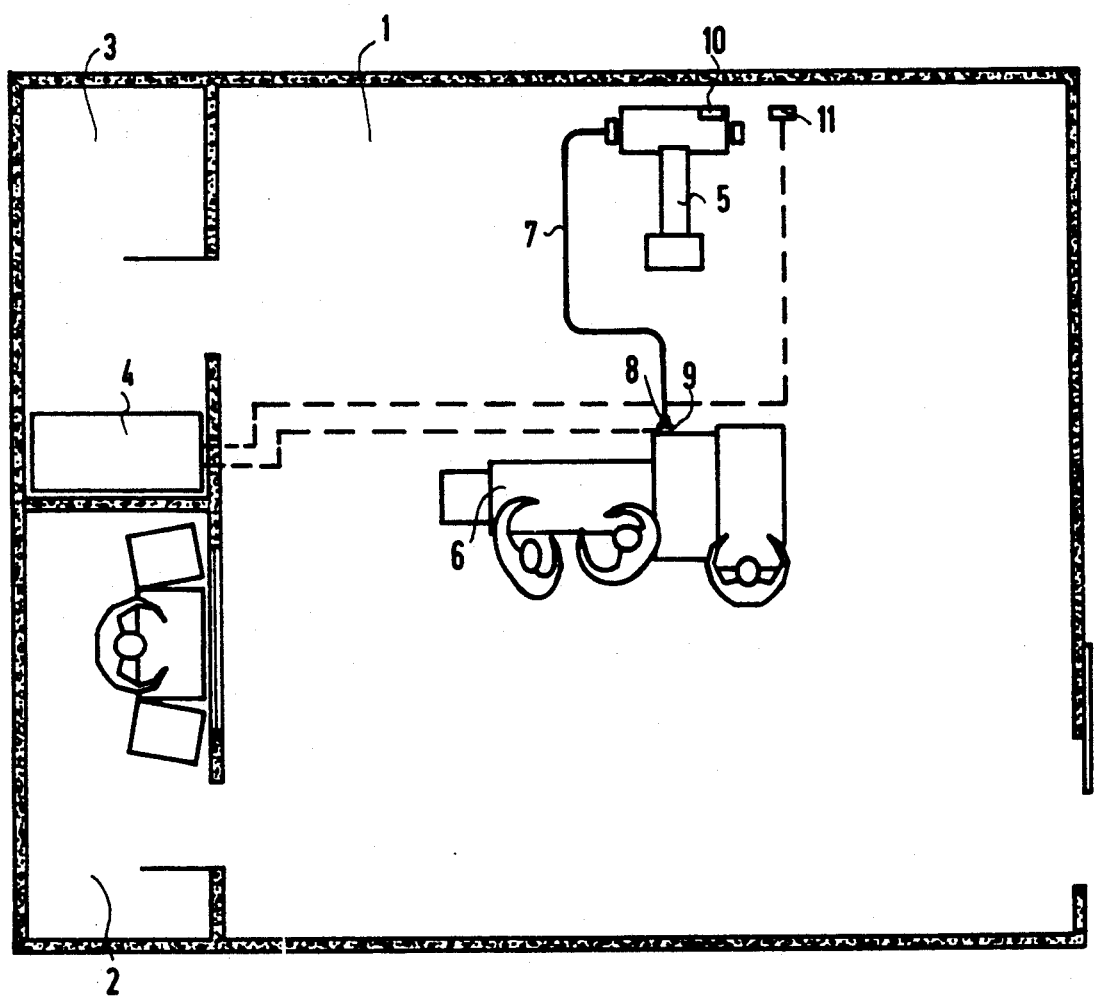

X-RAY DIAGNOSTICS INSTALLATION

This is a continuation of application Ser. No. 624,572, filed Dec. 10, 1990, now abandoned.

BACKGROUND OF THE INVENTION

1. Field of the Invention

The present invention relates to an x-ray diagnostic installation having a portable x-ray apparatus, including an image pick-up device for generating image data, and image electronics.

2. Description of the Prior Art

In the operation of a portable x-ray apparatus such as a C-bend apparatus, it is customary to accommodate the image electronics in a truck, connected to the x-ray apparatus via a fixed cable. Thus, the image electronics must also be proximally placed in relation to the x-ray apparatus, or excessive or disturbing cable lengths will be necessary to connect the x-ray means to the image electronics.

SUMMARY OF THE INVENTION

It is an object of the present invention to provide an x-ray diagnostic installation having the image electronics arranged separately from the x-ray apparatus, such that the image electronics and x-ray apparatus are not connected with cables that cause disturbances during the examination mode of the electronics image.

The above-stated object is achieved in a data transmission link for transmitting image data, having a data coupling, wherein the data coupling is partially allocated to the x-ray apparatus and partially allocated to the image electronics. The data coupling can be formed by a data socket and an allocated data plug, where these components are connected via a fixed underground cable, leading from the patient bearing table to the image electronics and a further cable leading to the x-ray apparatus.

It is further contemplated that a wireless data transmitter at the x-ray apparatus be provided with a stationary or mobile data receiver allocated in the examination room, where a data cable leading to the image electronics is extended from the data receiver. The data receiver can be arranged within the housing of the image electronics upon construction of the image electronics such that disturbance-free data transmission is guaranteed.

Advantageously, an x-ray diagnostic installation, constructed in accordance with the principles of the present invention provides for an x-ray examination room which is largely free of data cables, such that cables prove disturbing to attempts to move x-ray apparatus are removed therefrom.

BRIEF DESCRIPTION OF THE DRAWINGS

FIG. 1 is an exemplary embodiment of an x-ray diagnostic installation constructed in accordance with the principles of the present invention.

DESCRIPTION OF THE PREFERRED EMBODIMENTS

As illustrated in FIG. 1, the floor plan of an x-ray examination room 1 includes a measuring and monitoring room 2 and a computer room 3 for housing the image electronics 4. A portable x-ray apparatus 5, such as a C-bend apparatus, may be used in the examination room 1 for obtaining x-ray images of a patient on a patient bearing table 6. For example, the x-ray apparatus 5 has an image intensifier video chain for generating image data.

Image data may be transmitted via a data cable 7 to a data plug 8, the data plug 8 being plugged into a data socket 9 at the patient bearing table 6. A fixed underground cable leading from the data socket 9 to the image electronics 4 is illustrated via the dotted lines of FIG. 1. Thus, a free adjustment of the x-ray examination apparatus 5 into, for example, a standby position, is possible by separating the data coupling of components 8 and 9.

It is further contemplated that the image data may be transmitted by the use of a wireless transmitter, such as an optical transmitter 10, embodiment within the portable x-ray apparatus 5, to which a receiver 11 at the ceiling of the examination room 1 is allocated. The receiver 11 is connected via permanently fixed cables in the ceiling of the examination room 1 and lead from the receiver 11 to the image electronics 4, allowing for full portability of the x-ray examination apparatus 5.

Although other modifications and changes may be suggested by those skilled in the art, it is the intention of the inventors to embody within the patent warranted hereon all changes and modifications as reasonably and properly come within the scope of their contribution to the art.

We claim:

1. An x-ray diagnostic installation comprising:
   mobile x-ray means, including image intensifier video chain means for generating image data of said patient, movable on the floor of a patient examination room, for exposing a patient in said examination room to x-rays;
   image electronic means for accepting image data of said patient from x-rays attenuated by said patient, said image electronic means being spatially separated from said x-ray means, wherein said image electronic means includes means for displaying said image data of said patient; and
   mechanically releasable data transmission means, selectively connecting said mobile x-ray means to said image electronic means, for transmitting said image data between said x-ray means and said image electronic means.

2. The x-ray diagnostic installation of claim 1, further comprising a flexible data cable connecting said x-ray means to a data plug mechanism, a patient bearing table to which said data plug mechanism is connected, and a permanently installed data cable connected to said image electronic means and to said patient bearing table.

3. The x-ray diagnostic installation of claim 1, further comprising a wireless transmitter connected to said x-ray means, receiver means, disposed in an examination room in which said examination subject is located, for transmitting image data from said wireless transmitter to said receiver means, and a data cable electrically connecting said receiver means to said image electronic means.

4. The x-ray diagnostic installation of claim 3, wherein said receiver means is fixedly located in the examination room.

5. An x-ray diagnostic installation according to claim 1, said transmission means further comprising a data coupling, including a data plug and a data socket, said data plug being connected to said x-ray means and said data socket being connected to said image electronic means.

6. An x-ray diagnostic installation according to claim 1, said transmission means further comprising a data coupling, including a data plug and a data socket, said data plug being electrically connected to said image electronic means and said data socket being electrically connected to said x-ray means.

7. An x-ray diagnostic installation comprising:
mobile x-ray means for exposing an examination subject to x-rays, including an image intensifier video chain for generating image data of said examination subject from x-rays attenuated by said examination subject;
image electronic means for accepting said image data, said image electronic means being spatially separated from said x-ray means; and
detachable data transmission means, selectively connecting said x-ray means to said image electronic means, for transmitting said image data between said x-ray means and said image electronic means.

8. An x-ray diagnostic installation comprising:
mobile x-ray means, including image intensifier video chain means for generating image data of said examination subject, for exposing an examination subject to x-rays, movable along a floor of an examination room;
image electronic means for accepting image data of said examination subject from x-rays attenuated by said examination subject, said image electronic means being spatially separated from said x-ray means; and
mechanically releasable data transmission means, selectively connecting said mobile x-ray means to said image electronic means, for transmitting said image data between said x-ray means and said image electronic means.

* * * * *